US009098892B2

(12) United States Patent
Deslandes et al.

(10) Patent No.: US 9,098,892 B2
(45) Date of Patent: Aug. 4, 2015

(54) LOCK IN THERMAL LASER STIMULATION THROUGH ONE SIDE OF THE DEVICE WHILE ACQUIRING LOCK-IN THERMAL EMISSION IMAGES ON THE OPPOSITE SIDE

(71) Applicant: DCG Systems, Inc., Fremont, CA (US)

(72) Inventors: Herve Deslandes, Saint Martin d'Uriage (FR); Rudolf Schlangen, San Francisco, CA (US); Prasad Sabbineni, San Ramon, CA (US); Antoine Reverdy, Grenoble (FR); Ingrid De Wolf, Leuven (BE)

(73) Assignee: DCG SYSTEMS, INC., Fremont, CA (US)

( * ) Notice: Subject to any disclaimer, the term of this patent is extended or adjusted under 35 U.S.C. 154(b) by 0 days.

(21) Appl. No.: 14/243,859

(22) Filed: Apr. 2, 2014

(65) Prior Publication Data
US 2014/0210994 A1 Jul. 31, 2014

Related U.S. Application Data

(62) Division of application No. 13/280,260, filed on Oct. 24, 2011.

(60) Provisional application No. 61/406,060, filed on Oct. 22, 2010.

(51) Int. Cl.
*H04N 7/18* (2006.01)
*G06T 7/00* (2006.01)
(Continued)

(52) U.S. Cl.
CPC ............. *G06T 7/0008* (2013.01); *G01N 25/72* (2013.01); *G01R 31/311* (2013.01); *G01R 35/005* (2013.01); *H04N 5/33* (2013.01)

(58) Field of Classification Search
CPC .... G06T 7/0008; G01N 25/72; G01R 31/311; G01R 35/005; H04N 5/33

USPC .......................................................... 348/92
See application file for complete search history.

(56) References Cited

U.S. PATENT DOCUMENTS 4,557,607 A 12/1985 Busse
4,950,897 A 8/1990 Mandelis et al.
(Continued)

FOREIGN PATENT DOCUMENTS

CN 1696674 A 11/2005
CN 103026216 A 4/2013
(Continued)

OTHER PUBLICATIONS

Altmann, F. et al., "Characterization and Failure Analysis of 3D Integrated Semiconductor Devices-Novel Tools for Fault Isolation, Target Preparation and High Resolution Material Analysis," ISTFA 2010: Proceedings of the 36th International Symposium for Testing and Failure Analysis (ASM International), Fraunhofer Institute for Mechanics of Materials, Halle, Germany, Nov. 1, 2010, pp. 163-170.
(Continued)

*Primary Examiner* — Allen Wong
(74) *Attorney, Agent, or Firm* — Nixon Peabody LLP; Joseph Bach, Esq.

(57) ABSTRACT

Controlled amount of heat is injected into a stacked die using a light beam, and the propagated heat is measuring with LIT camera from the other side of the die. The thermal image obtained can be characterized so that it can be used to calibrate the phase shift from a given stack layer, or can be used to identify defects in the stacked die. The process can be repeated for each die in the stack to generate a reference for future testing. The thermal image can be investigated to detect faults, such as voids in vias, e.g., TSV.

18 Claims, 2 Drawing Sheets

(51) Int. Cl.
*G01N 25/72* (2006.01)
*G01R 31/311* (2006.01)
*G01R 35/00* (2006.01)
*H04N 5/33* (2006.01)

(56) References Cited

U.S. PATENT DOCUMENTS

| | | |
|---|---|---|
| 5,667,300 A | 9/1997 | Mandelis et al. |
| 6,399,948 B1 | 6/2002 | Thomas et al. |
| 6,759,659 B2 | 7/2004 | Thomas et al. |
| 6,786,098 B2 | 9/2004 | Bates |
| 6,812,468 B1 | 11/2004 | Baumann et al. |
| 6,840,667 B2 | 1/2005 | Schlagheck et al. |
| 7,018,094 B1 | 3/2006 | Bates |
| 7,131,331 B2 | 11/2006 | Bates |
| 7,272,207 B1 | 9/2007 | Aufrichtig et al. |
| 7,429,735 B2 | 9/2008 | Lueerssen et al. |
| 7,444,260 B2 | 10/2008 | Raad |
| 7,554,086 B2 | 6/2009 | Shepard et al. |
| 7,709,794 B2 | 5/2010 | Zhao et al. |
| 8,306,608 B2 | 11/2012 | Mandelis et al. |
| 8,742,347 B2 | 6/2014 | Altmann et al. |
| 9,025,020 B2 | 5/2015 | Deslandes et al. |
| 2002/0172410 A1 | 11/2002 | Shepard |
| 2003/0137318 A1 | 7/2003 | Enachescu et al. |
| 2005/0008215 A1 | 1/2005 | Shepard |
| 2005/0056786 A1 | 3/2005 | Shepard et al. |
| 2006/0140445 A1 | 6/2006 | Cusack |
| 2007/0021670 A1 | 1/2007 | Mandelis et al. |
| 2009/0201971 A1 | 8/2009 | Goldammer et al. |
| 2009/0245322 A1 | 10/2009 | Hudgings et al. |
| 2009/0297017 A1 | 12/2009 | Hudgings et al. |
| 2010/0062550 A1 | 3/2010 | Buchel et al. |
| 2010/0073665 A1 | 3/2010 | Zhao et al. |
| 2010/0074515 A1 | 3/2010 | Zhao et al. |
| 2010/0091812 A1 | 4/2010 | Louban et al. |
| 2010/0163732 A1 | 7/2010 | Louban et al. |
| 2011/0297829 A1 | 12/2011 | Altmann et al. |
| 2012/0098957 A1 | 4/2012 | Deslandes et al. |
| 2014/0346360 A1 | 11/2014 | Altmann et al. |

FOREIGN PATENT DOCUMENTS

| | | |
|---|---|---|
| DE | 4203272 A1 | 8/1993 |
| DE | 19838858 A1 | 4/1999 |
| DE | 19835616 A1 | 2/2000 |
| DE | 19835616 C2 | 2/2002 |
| DE | 10053112 A1 | 5/2002 |
| DE | 10059854 A1 | 6/2002 |
| DE | 10150633 A1 | 4/2003 |
| DE | 60016939 T2 | 12/2005 |
| DE | 10 2005 053 203 A1 | 5/2007 |
| DE | 10 2006 043 339 A1 | 3/2008 |
| DE | 10 2007 037 377 A1 | 2/2009 |
| DE | 10 2007 058 566 A1 | 6/2009 |
| EP | 1 852 697 A1 | 11/2007 |
| EP | 2 444 795 A1 | 4/2012 |
| EP | 2 580 583 A1 | 4/2013 |
| JP | 2004-069439 A | 3/2004 |
| JP | 2012-093355 A | 5/2012 |
| JP | 2013-526723 A | 6/2013 |
| JP | 5631484 B2 | 10/2014 |
| JP | 2014-222243 A | 11/2014 |
| KR | 2013-0087487 A | 8/2013 |
| SG | 180133 A1 | 5/2012 |
| SG | 186207 A1 | 1/2013 |
| TW | 201215881 A1 | 4/2012 |
| TW | 201229504 A1 | 7/2012 |
| WO | 01/29545 A1 | 4/2001 |
| WO | 2007/147158 A2 | 12/2007 |
| WO | 2010/099964 A3 | 9/2010 |
| WO | 2011/156527 A1 | 12/2011 |

OTHER PUBLICATIONS

Breitenstein, O. et al., Lock-in Thermography: Basics and Use for Evaluating Electronic Devices and Materials Series, Springer Series in Advanced Microelectronics, vol. 10, 2nd ed., 2010, X, 258 pages.

Breitenstein, O., et al., "Unusual Lock-In Thermography Signals: Schottky-Type Grid Contacts, Peltier Effects, and Thermal Wave Interference," IV World Conference on Photovoltaic Energy Conversion, May 7-12, 2006, Waikaloa, Hawaii, pp. 912-915.

Dillenz, A., "Progress in Phase Angle Thermography," Review of Scientific Instruments, AIP, Melville, NY, US, vol. 74, No. 1, Jan. 1, 2003, pp. 417-419.

Dorr, P., "Multi-Parameter-Fitting Procedure for Photothermal Infrared Radiometry on Multilayered and Bulk-Absorbing Solids," Journal of Applied Physics, American Institute of Physics, New York, US, vol. 89, No. 12, Jun. 15, 2001, pp. 7888-7894.

Junyan, L., "Research on Thermal Wave Processing of Lock-in Thermography Based on Analyzing Image Sequences for NDT," Infrared Physics & Technology, Elsevier Science B.V. Netherlands, vol. 53, No. 5, Sep. 2010, pp. 348-357.

Liu, H. et al., "Effect of Modulation Frequency on Detecting Defects of Metal Plates Using Infrared Lock-in Thermography," Proceedings of SPIE—The International Society of Optical Engineering—4th International Symposium on Advanced Optical Manufacturing and Testing Technologies: Optical Test and Measurement Technology and Equipment 2009 SPIE USA, vol. 7283, Nov. 19, 2008, pp. 72833M-1 to 72833M-7.

Maldague, X., "Active Thermography," Theory and Practice of Infrared Technology for Nondestructive Testing, Wiley, John & Sons, Incorporated, Chapter 9, Apr. 2001, pp. 343-365.

Schmidt, C., et al., "Application of Lock-in-Thermography for 3D Defect Localisation in Complex Devices", 2nd Electronics Systemintegration Technology Conference, 2008. 2nd IEEE, Piscataway, NJ, USA, Sep. 1, 2008, pp. 1041-1044.

Schmidt, C., "Localization of Electrical Defects in System in Package Devices Using Lock-in Thermography", Electronic System-Integration Technology Conference (ESTC), 2010 3rd, IEEE, Piscataway, NJ, USA, Sep. 13, 2010, pp. 1-5.

Schmidt, C. et al., "Lock-in-Thermography for 3-Dimensional Localization of Electrical Defects Inside Complex Packaged Devices", Conference Proceedings from the International Symposium for Testing and Failure Analysis (34th International Symposium for Testing and Failure Analysis, ISTFA) Nov. 2-6, 2008, Jan. 1, 2008, pp. 102-107.

Schmidt, C. et al., "Non-Destructive Defect Depth Determination at Fully Packaged and Stacked Die Devices Using Lock-in Thermography", Physical and Failure Analysis of Intergrated Circuits (IPFA), 2010, 17th IEEE International Symposium, IEEE, Piscataway, NJ, USA, Jul. 5, 2010, pp. 1-5.

Schmidt, C., et al., "Thermal Simulation of Defect Localization Using Lock-in Thermography in Complex and Fully Packaged Devices," Thermal, Mechincal and Mutli-Physics Simulation and Experiments in Microelectronics and Microsystems, Eurosime 2009, 10th International Conference ON, IEEE, Piscataway, NJ, USA, Apr. 26, 2009, pp. 1-7.

Tarin, M., et al., "Fuselage Inspection of Boeing-737 Using Lock-in Thermography," The International Society for Optical Engineering SPIE, Proceedings of the SPIE—Thermosense XXX, Mar. 18-20, 2008, Orlando, FL, USA, vol. 6939, pp. 693919-1 to 693919-10.

"Heat Flux Thermography: From Laboratory System to Industrial Application," Thermosensorik GmbH, Germany, May 1, 2009, Inspect-Online, available at http://www.inspect-online.com/en/topstories/control/heat-flux-thermography, retrieved Oct. 11, 2011.

Office Action in U.S. Appl. No. 13/156,289, mailed on Aug. 24, 2012.
Office Action in U.S. Appl. No. 13/156,289, mailed on Apr. 3, 2013.
Notice of Allowance in U.S. Appl. No. 13/156,289, mailed on Jan. 16, 2014.
Office Action in U.S. Appl. No. 13/280,260, mailed on Dec. 27, 2013.
Office Action in U.S. Appl. No. 13/280,260, mailed on Jun. 16, 2014.

(56) References Cited

OTHER PUBLICATIONS

Extended European Search Report in European Application No. 11185795.9, mailed on Feb. 17, 2012.
Examination Report in European Patent Application No. 11185795.9, dated Jun. 16, 2014.
First Office Action for Chinese Patent Application No. 201180036274.0, dated Mar. 4, 2014.
Office Action in Japanese Patent Application No. 2013-512069, dated Nov. 5, 2013.
Notice of Decision of Refusal for Japanese Patent Application No. 2013-512069, dated Mar. 28, 2014.
Notice of Decision to Grant Japanese Patent Application No. 2013-512069, dated Sep. 30, 2014.
Examination and Search Report in Taiwanese Patent Application No. 100119928, mailed on Apr. 15, 2014.
Examination Report in Taiwanese Patent Application No. 100137995, mailed on Apr. 22, 2014.
PCT International Search Report and Written Opinion in International Application No. PCT/US2011/039679, mailed on Sep. 20, 2011.
PCT International Preliminary Report on Patentability in International Application No. PCT/US2011/039679, mailed on Dec. 20, 2012.
PCT International Search Report and Written Opinion in International Application No. PCT/EP2012/074982, mailed on Apr. 8, 2013.
Notice of Allowance in U.S. Appl. No. 13/280,260 dated Jan. 2, 2015.
Second Office Action for Chinese Patent Application No. 201180036274.0, dated Nov. 25, 2014.
Notice of Allowance of Taiwanese Patent Application No. 100119928 dated Sep. 24, 2014.
Notice of Allowance of Taiwanese Patent Application No. 100137995 dated Jul. 30, 2014.
Office Action for U.S. Appl. No. 14/294,016 dated Apr. 23, 2015.

LOCK IN THERMAL LASER STIMULATION THROUGH ONE SIDE OF THE DEVICE WHILE ACQUIRING LOCK-IN THERMAL EMISSION IMAGES ON THE OPPOSITE SIDE

RELATED APPLICATIONS

This application is a divisional of U.S. patent application Ser. No. 13/280,260, filed on Oct. 24, 2011, which claims priority benefit from U.S. Provisional Application No. 61/406,060, filed on Oct. 22, 2010, the disclosures of which are incorporated herein by reference in their entireties.

BACKGROUND

1. Field of Invention

This invention is in the field of defect localization analysis of semiconductor devices and calibration apparatus and method for such defect localization.

2. Related Art

During design and verification stage of semiconductor devices, it is important to test for various defects or problematic areas of the chip design that may lead to defects. One class of defects are those causing localized heating of the chip. During the testing stage, it is important to identify such defects. One method for identifying localized heating defects is called Lock In Thermography (LIT). A current product available from the subject assignee, DCG Systems, Inc., of Fremont, Calif., uses this technique and is called ELITE™. The term LIT refers to a non destructive technique that detects very small heat variation across a sample, using a lock in amplifier. The system identifies and "localizes" i.e., provides the location coordinates of, defects causing localized heating inside the chip.

Another kind of testing done during design verification is called Thermal Laser Stimulation (TLS or SLS for static laser stimulation). A current product available from the subject assignee using this technique is the MERIDIAN™ or TriVision™. The term TLS refers to using a laser (e.g., 1340 nm wavelength) to create local heating on the semiconductor IC to test the effect of heating on the IC's performance. In such a system, the IC is coupled electrically to a tester and is provided with electrical test signals. A laser source is used to cause local heating and the tester is used to study the electrical response of the IC to such heating. That is, the IC's response to an electrical test signal with and without the laser heating can be compared by examining the electrical output of the IC. In conventional TLS, a continuous wave laser is used to induce heat in the device under test. This technique is used to detect metal shorts inside the device.

With the advancement in complex and stacked-die devices, it becomes increasingly difficult to test devices using traditional techniques. Also, a recent stacked die architecture employs a structure called Through-Silicon Via (TSV). Since TSV have high aspect ratio, it is difficult to evenly fill them with conductive material. However, improperly filled TSV may lead to device performance degradation or even malfunction. Accordingly, new and improved techniques and apparatus are needed to assist in testing such devices.

SUMMARY

The following summary is included in order to provide a basic understanding of some aspects and features of the disclosure. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

According to aspects of the invention, controlled amount of heat is injected into a stacked die using a light beam, and the propagated heat is measuring with a thermal sensor from the other side of the die. The thermal image obtained can be characterized so that it can be used to calibrate the phase shift from a given stack layer, or can be used to identify defects in the stacked die. The process can be repeated for each die in the stack to generate a reference for future testing. The thermal image can be investigated to detect faults, such as voids in vias, e.g., TSV.

According to aspects of the invention, a system for analysis of a device under test (DUT) is provided, comprising: a test bench to support the DUT; a heat source position to deliver a prescribed amount of energy to a localized spot the DUT from one side thereof; a thermal imaging system positioned so as to image the other side of DUT; and, a controller activating said heat source to deliver the prescribed amount of energy and receiving output signal from said thermal imaging system. The heat source may comprise a light source, such as a laser light source. According to disclosed embodiments, the controller activates the light source at a lock-in frequency f1, and activates the thermal imaging system at a lock-in frequency f2. The lock-in frequency f2 may be at least four times higher than lock-in frequency f1. The thermal imaging system may comprise an infrared camera and the heat source may further comprise: a movable stage; an optical scanner coupled to the movable stage, the optical scanner receiving output of the light source and directing the output to a specified spot on the DUT; and, an objective lens focusing the output onto a the specified spot on the DUT.

According to further aspects, a system for analysis of a device under test (DUT) is disclosed, comprising: a test bench to support the DUT; a lock-in laser light source operating at a lock-in frequency f1 and position to deliver a pulsed laser light beam onto the DUT from one side thereof; a lock-in thermal imaging system operating at a lock-in frequency f2 and positioned so as to image the other side of DUT; and, a controller activating the heat source at the lock-in frequency f1 and activating said thermal imaging system at the lock-in frequency f2. In disclosed embodiments, the controller outputs a lock-in frequency f1 trigger signal to the lock-in laser light source and outputs a lock-in frequency f2 trigger signal to the lock-in thermal imaging system, wherein the lock-in frequency f2 is at least four times larger than lock-in frequency f1. The lock-in laser light source may comprise: an excitation source receiving the lock-in frequency f1 trigger signal and generating pulsed laser light beam; a scan unit receiving and directing the pulsed laser light beam onto a defined location on the DUT; and, an objective lens focusing the pulsed laser light beam onto the defined location. The lock-in thermal imaging system may comprise an infrared camera.

According to yet further aspects, a method for testing a device under test (DUT) is provided, comprising: situating the DUT onto a test bench; illuminating a defined spot on one side of the DUT; obtaining a thermal image of the other side of the DUT; and, analyzing the thermal image to thereby characterize the thermal propagation of heat within the DUT. Illuminating a defined spot may comprise delivering a series of laser light pulses at a frequency f1, and obtaining a thermal image may comprise obtaining a series of images at a frequency f2. The method may further comprise synchronizing frequencies f1 and f2, wherein frequency f2 is at least four times higher than frequency f1. The method may further comprise focusing the series of pulses into a predefined depth within the DUT. The defined spot may includes at least one through-silicon via (TSV), and the method may further comprise comparing the thermal image to a reference thermal image to thereby investigate faults in the TSV. The method may further comprise assembling a reference database of thermal propagation of heat within various layers of the DUT.

BRIEF DESCRIPTION OF THE DRAWINGS

Other aspects and features of the invention would be apparent from the detailed description, which is made with reference to the following drawings. It should be appreciated that the detailed description and the drawings provides various non-limiting examples of various embodiments of the invention, which is defined by the appended claims.

The accompanying drawings, which are incorporated in and constitute a part of this specification, exemplify various embodiments and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements and are, therefore, not drawn to scale.

DETAILED DESCRIPTION

Embodiments of this invention enable thermal defect analysis using a micrometer spot size heat source and create calibration methods for IC's and stacked dies analysis. According to embodiments of the invention, light source, such as laser, laser diode, etc., is used to generate local heating inside the die. The local heating is studied using, e.g., thermal emission image acquisition from the opposite side of the die.

According to embodiments of the invention, the lock in thermal laser stimulation is combined along with the lock in thermal emission to study the IC design. One technique works from one side of the device and the other technique from the opposite side simultaneously and synchronously.

According to one embodiment, laser pulses (e.g., 1340 nm wavelength or any wavelength above 1064 nm, which is the silicon bandgap) are directed at a given location of the IC at a given lock-in frequency, thereby causing localized heating inside the IC. The optical system, i.e., objective lenses etc., can be used to focus the beam at any depth inside the IC. The heat is detected from the opposite side by the thermal, e.g., infrared (IR), camera. The thermal camera is also operating in a lock-in mode. The camera operating frequency is at least 4 times higher compared to the laser lock-in frequency (in accordance with the Nyquist-Shannon sampling theorem). The fact that both systems work in lock-in mode enables much higher sensitivity.

This technique can be used for the calibration process of the heat propagation through a stacked die and specifically the phase shift analysis. During traditional LIT testing, the excitation source is a power supply applying electrical signal to the IC. The localized heat is generated inside a stacked die because of a physical defect, and is detected at the IC's surface by the LIT system using a thermal sensor. The heat wave propagating through the various layers of the IC has a phase shift with respect to the power supply phase. The amount of phase shift will depend on the type of materials between the defect and the surface and the depth of the defect inside the IC. However, generally the correlation of the amount of phase shift to the type of material and defect depth is not known. Thus, in the prior art it is difficult to determine the depth of the defect within the IC.

Embodiments of the inventive method utilize injecting controlled heat on the stacked die and measuring it's heat propagation with the thermal camera, so that it can be used to calibrate the phase shift from a given stack layer. This can be repeated for each die in the stack to generate a reference for future testing. This can also be done by physically removing each die one by one and performing the phase measurement for each one of them.

Figure 1:
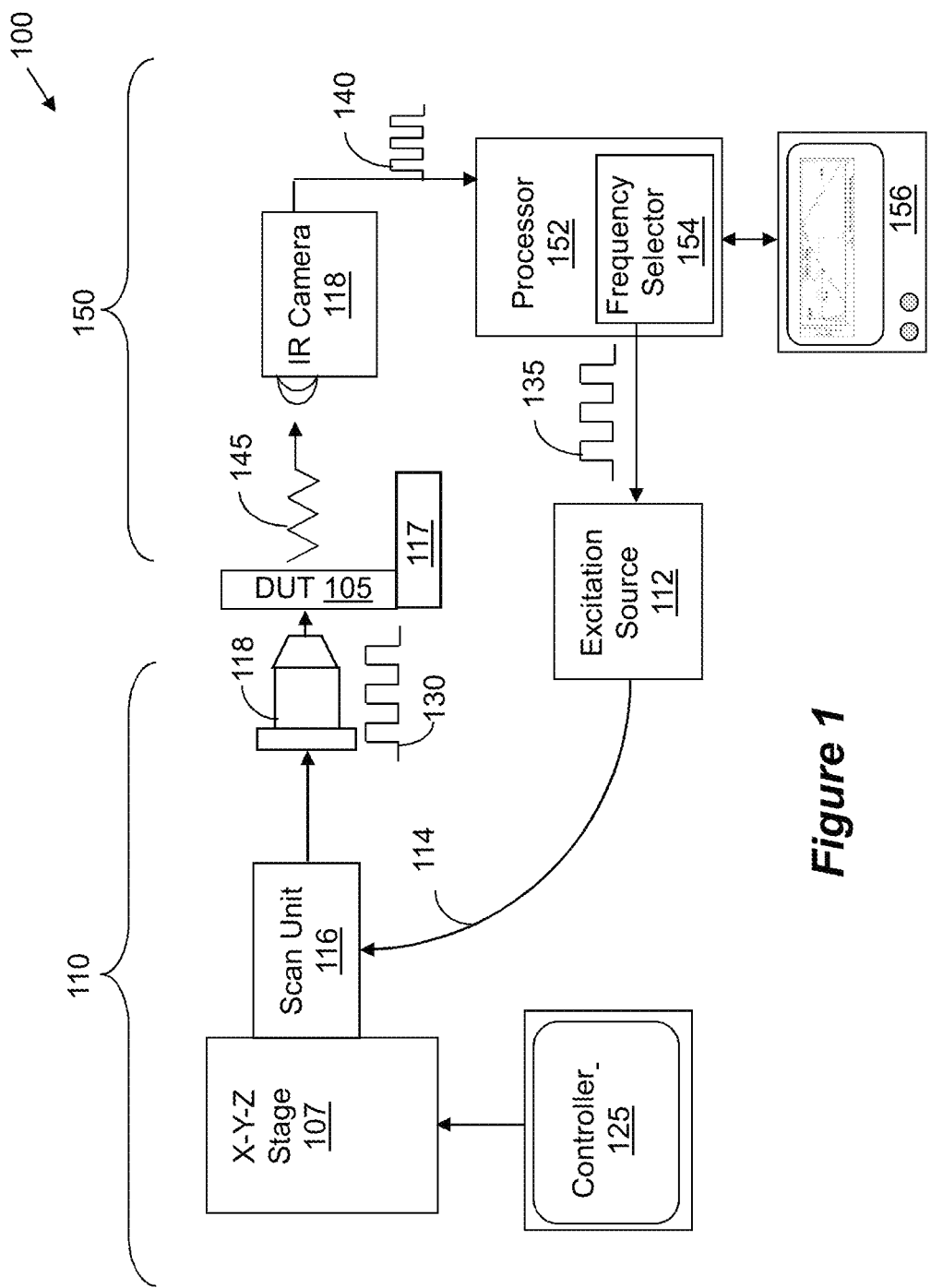
FIG. 1 illustrates an embodiment of the invention showing an arrangement for testing IC device.

FIG. 1 illustrates an embodiment of the invention showing an arrangement 100 for testing IC device under test, DUT 105. The arrangement 100 includes a test bench 117 that supports the DUT 105, an optical heat source 110 position to illuminate the DUT 105 from one side thereof, and a thermal imaging system 150 positioned so as to image the other side of DUT 105. The optical heat source 110 utilizes a light source 112, e.g., a laser, a laser diode, etc., to deliver a predetermined amount of energy into a selected location inside the DUT 105. In the illustration of FIG. 1, the light source 112 delivers pulses of light to a scanner 116, each pulse being of a set duration and intensity calculated to deliver the required amount of energy. The scanner 116 is operated to direct the light pulses to a selected location on the DUT 105. That is, the scanner 116 is not operated in a scanning mode, i.e., it does not scan the DUT 105, but is rather used in a static mode to direct the light pulses to a single selected location. The light pulses are focused onto the DUT 105 by the objective 118.

As the light pulses are being focus at a selected location on the DUT 105, a hot spot is generated within the DUT 105. The propagation of the hot spot towards the other surface of the DUT 105 is dependent on the material and thickness of the various layers between the hot spot location and the back surface of the DUT 105. Once the heat propagates to the back surface, thermal emission 145 is imaged by thermal sensor, e.g., IR camera 118. The IR camera 118 is operated in a lock-in mode, controlled by processor 152. To improve accuracy, in this embodiment the lock-in frequency 140 of the camera 118 is set to at least four times the lock-in frequency 135 of the light source 112. The thermal images are then analyzed so as to characterize the thermal propagation within the DUT 105. This characterization can be used for localizing hot spots within the DUT 105, which are caused by defects or faulty design of the DUT 105. For example, electrical test signals can be applied to the DUT 105, while performing thermal imaging of the surface of the DUT 105. The electrical test signal would cause defects to generate hot spots, which can be imaged using the thermal imaging. The characterization can be used to determine the precise depth of the defect within the DUT 105.

Figure 2:
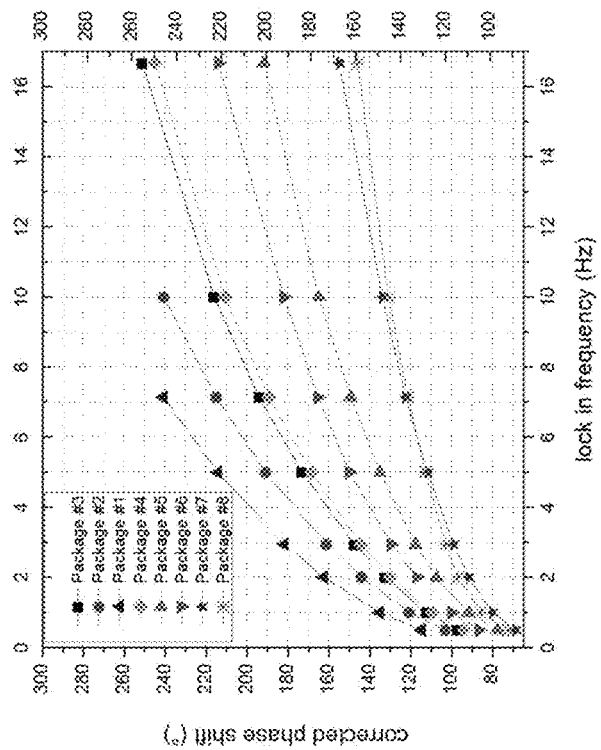
FIG. 2 shows the result of the experiment for an 8-die stack.

FIG. 2 shows the result of an experiment for an 8-die stack. The curves of FIG. 2 illustrate the calibrated phase vs. lock-in frequency for each of the layers. These curves can be used for LIT testing of devices having similar structures.

According to another example, a system such as illustrated in FIG. 1 can be used for the localization of defective TSVs (Through-Silicon Via). During fabrication, all TSV's on the device should be properly filled with conductive material in order to properly conduct the electrical signals. Any void in any TSV needs to be detected, as it will increase the resistance of the TSV, causing reduced performance or failure of the IC. Coincidentally, any void in a TSV will also slow down or prevent the propagation of the heat from a defect or from excitation source 112. Therefore, according to an embodiment of the invention, the excitation source 112 is used to cause hot spot on one side of the die, to generate heat propagation to the other side, where a thermal emission camera is positioned to image the surface of the die. Heat propagation within a properly structured TSV, which can be set as a reference TSV, can be compared to heat propagation in a TSV under test. If heat propagation is slower or heat transfer is lower, i.e., thermal image is fainter, it would signify a defective TSV.

Figure 3:
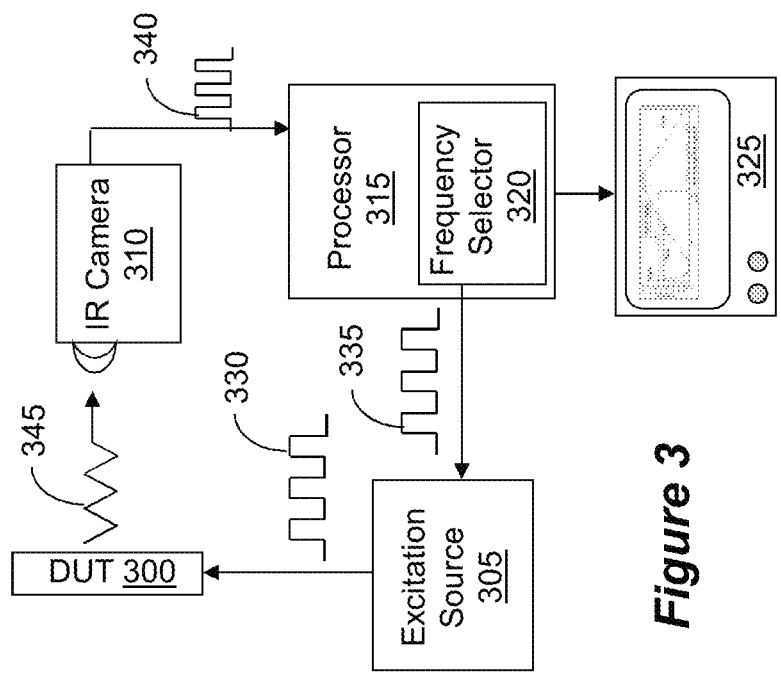
FIG. 3 illustrates an embodiment for testing the DUT after the thermal propagation characteristics have been established.

FIG. 3 illustrates an embodiment for testing the DUT 300 after the thermal propagation characteristics have been established. DUT 300 is stimulated by electrical excitation signal 330 at frequency f0 generated by electrical excitation source 305. In one example the excitation signal 330 is a square wave having amplitude voltage equal to the DUT's operational voltage, e.g., 1.2 V, and a lock-in frequency f0. The frequency f0 of the excitation signal is set and varied by frequency selector part 320, of processor 315. A sync signal 335 is output from the processor 315 and sent to the excitation source 305. The simplest arrangement is to set the sync signal 335 at the same frequency f0, although it may be a different frequency, so long as provisions are made to enable excitation source 305 to generate the electrical excitation signal 330 at frequency f0. An IR camera 310 is used to snap IR images of selected area of the DUT 300. The frame rate of camera 310 is usually but not exclusively set to be higher than the frequency f0. Here it is set to at least four times higher than frequency f0. This operation can also be handled by an automated testing equipment (ATE), i.e., the ATE sends the drive signal to the DUT and at the same time sends a trigger signal to the controller and the camera.

With the setup of FIG. 3, the DUT 300 is repeatedly excited by excitation source 305, while the frequency f0 of the excitation signal is varied according to the sync signal 335 provided by the frequency selector 320. This enables a better and more accurate identification of a hot spot's location, especially its depth (i.e. z direction) within the electronic device. Additionally, the setup of FIG. 3 does not output a single phase data point, but rather enables plotting the entire response curve on monitor 325. Having the entire response curve enables further analysis, such as curve fitting to better understand the time-resolved heat dissipation within the DUT. Notably, as can be appreciated, unlike standard debug methods, such as OBIC, LVP, TREM, etc., which require de-capsulation of the device and thinning the backside of the chip, with the setup of FIG. 3, the test is done without having to de-capsulate the chip.

For three-dimensional hot spot localization inside of stacked die integrated devices, e.g., a system-in-package, a second factor of influence has to be regarded. Thermal waves generated at the hot spot position have to propagate through different material layers, e.g., silicon, mould compound, die attach tape, etc., each having different thicknesses. As a consequence, depending on the axial hot spot position at different dies of the defective device, not only the distance to the device surface but also the thermal diffusion length is changing. Therefore, thermal waves generated at hot spots at lower dies inside of the stack have to pass additional material layers compared to thermal waves generated at hot spots which are close to the device surface. This behavior can be used for the determination of the hot spot depth by calculating the theoretical phase shift over a certain frequency range for different hot spot positions. On the other hand, using the system and method disclosed herein, one can generate a database of thermal propagation characteristics of different layers or different devices and use the database as a reference to decipher defect depth of a tested device.

As can be understood from the above, disclosed embodiments enable the use of Lock-in Thermography for quantitative and non destructive 3D localization of hot spots i.e. generated by electrical structures or defects inside of electronic devices. The relationship between the applied lock-in frequency and the phase shift can be determined based on the characterization of thermal propagation in various tested devices and layers. This can be done for the case where a hot spot is buried under a single material layer of unknown thickness and for the case of a hot spot buried under an unknown number of dies inside of a stacked die device. The disclose method enables localization in all three dimensions of buried hot spots even under a thick layer of mould compound.

Furthermore, different die layers of system in package architectures could be measured, showing significant phase shift differences, allowing the exact determination of the defective die through the package. Despite the non-homogeneous material stack of stacked dies with complex thermal properties, constructing a database of thermal propagation characterization can enable exact localization of defects in such complex devices. The method of acquiring and analyzing these results for hot spot depth calculation is enabled by disclosed embodiments.

It should be understood that processes and techniques described herein are not inherently related to any particular apparatus and may be implemented by any suitable combination of components. Further, various types of general purpose devices may be used in accordance with the teachings described herein. It may also prove advantageous to construct specialized apparatus to perform the method steps described herein.

The present invention has been described in relation to particular examples, which are intended in all respects to be illustrative rather than restrictive. Those skilled in the art will appreciate that many different combinations of hardware, software, and firmware will be suitable for practicing the present invention. Moreover, other implementations of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for testing a device under test (DUT), comprising:
    situating the DUT onto a test bench, the DUT comprising a stack of a plurality of integrated circuits dies;
    illuminating a defined spot inside the DUT by directing a beam of pulsed laser source having wavelength above 1064 nm from one side of the DUT and focusing the beam onto a spot inside a selected one of the dies;
    obtaining a thermal images of the other side of the DUT; and,
    analyzing the thermal image to thereby characterize the thermal propagation of heat from the selected die through other dies within the DUT.

2. The method of claim 1, further comprising serially illuminating each one of the other dies to thereby generate a reference propagation for heat spot within each one of the dies.

3. The method of claim 2, further comprising generating a plot of calibrated phase vs. lock-in frequency for each of the dies.

4. The method of claim 2, further comprising applying electrical test signals to the DUT, while performing thermal imaging of the surface of the DUT.

5. The method of claim 4, further comprising comparing images obtained from the thermal imaging of the surface of the DUT to the reference propagation to determine the depth of a defect within the DUT.

6. The method of claim 4, further comprising comparing a phase obtained from the thermal imaging of the surface of the DUT to the plot of calibrated phase vs. lock-in frequency.

7. The method of claim 1, wherein the series of pulses is series of laser light pulses at a frequency f1, wherein obtaining a thermal image comprises obtaining a series of images at a frequency f2, and further comprising synchronizing frequencies f1 and f2.

8. The method of claim 7, wherein frequency f2 is at least four times higher than frequency f1.

9. The method of claim 7, further comprising applying electrical pulses to the DUT at frequency f1, while performing thermal imaging of the surface of the DUT.

10. The method of claim 9, wherein the electrical pulses comprise square wave having amplitude voltage equal to the DUT's operational voltage.

11. The method of claim 7, further comprising applying electrical pulses to the DUT, while performing thermal imaging of the surface of the DUT and varying the pulses' frequency.

12. A system for analysis of a device under test (DUT), the DUT comprising a plurality of stacked dies, comprising:
   a test bench to support the DUT;
   a lock-in laser light source operating at a lock-in frequency f1 and position to deliver a pulsed laser light beam onto the DUT from one side thereof;
   an objective lens arrangement operable to focus the pulsed laser light beam onto a selected die from the plurality of stacked dies;
   a lock-in thermal imaging system operating at a lock-in frequency f2 and positioned so as to image the other side of DUT; and,
   a controller activating said heat source at the lock-in frequency f1 and activating said thermal imaging system at the lock-in frequency f2, and for controlling the objective lens arrangement to successively focus the pulsed laser light beam onto a different dies from the plurality of stacked dies.

13. The system of claim 12, wherein the controller further generates a reference propagation for heat spot within each one of the dies.

14. The system of claim 13, further comprising means for applying electrical pulses to the DUT at frequency f1, while performing thermal imaging of the surface of the DUT.

15. The system of claim 14, wherein the controller further compares the thermal imaging of the surface of the DUT to the reference propagation.

16. The system of claim 13, further comprising means for applying electrical pulses to the DUT, while performing thermal imaging of the surface of the DUT and varying the pulses' frequency.

17. The system of claim 13, further comprising means for applying square wave pulses to the DUT while performing thermal imaging of the surface of the DUT, the square wave pulses having amplitude voltage equal to the DUT's operational voltage.

18. The system of claim 12, wherein the controller further generates a plot of calibrated phase vs. lock-in frequency for each of the dies.

* * * * *